United States Patent [19]
Rupp

[11] Patent Number: 5,593,387
[45] Date of Patent: Jan. 14, 1997

[54] NON-REUSABLE SYRINGE

[76] Inventor: Roberta N. Rupp, 126 Vinal St., Revere, Mass. 02151

[21] Appl. No.: 448,988

[22] Filed: May 24, 1995

Related U.S. Application Data

[63] Continuation-in-part of Ser. No. 204,810, Mar. 2, 1994, Pat. No. 5,419,773.

[51] Int. Cl.⁶ ..................................................... A61M 5/00
[52] U.S. Cl. .......................... 604/110; 604/220; 604/263
[58] Field of Search ..................................... 604/110, 187, 604/218, 220, 263

[56] References Cited

U.S. PATENT DOCUMENTS

| 4,932,941 | 6/1990 | Min et al. | 604/110 |
| 5,106,372 | 4/1992 | Ranford | 604/220 X |

Primary Examiner—John D. Yasko
Attorney, Agent, or Firm—Lorusso & Loud

[57] ABSTRACT

A non-reusable syringe with automatically actionable protective needle cover. The syringe consists of a syringe which locks the plunger in place after full injection, rendering it unusable. In addition an automatic needle cover is provided which aids as a clamping device and prevents pricking or leaking of a needle. the means of operating the needle cover also allows the needle to be visible for injection.

1 Claim, 8 Drawing Sheets

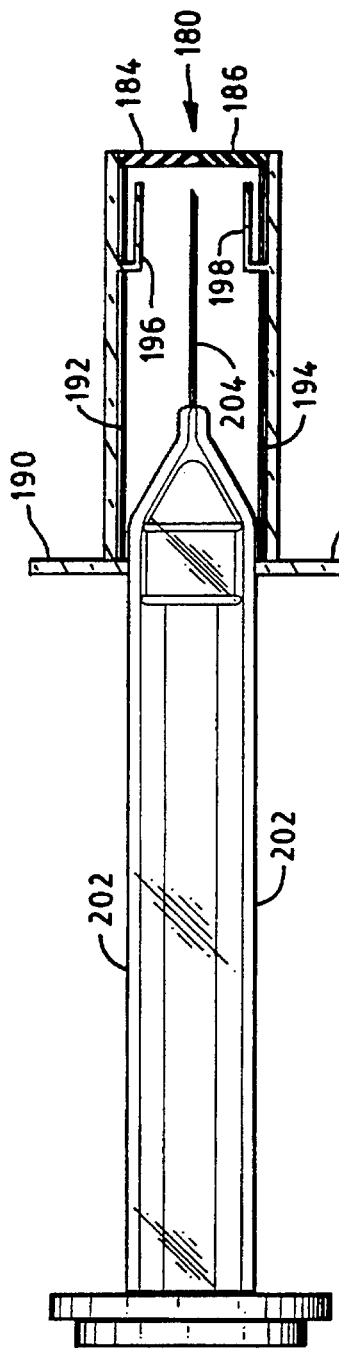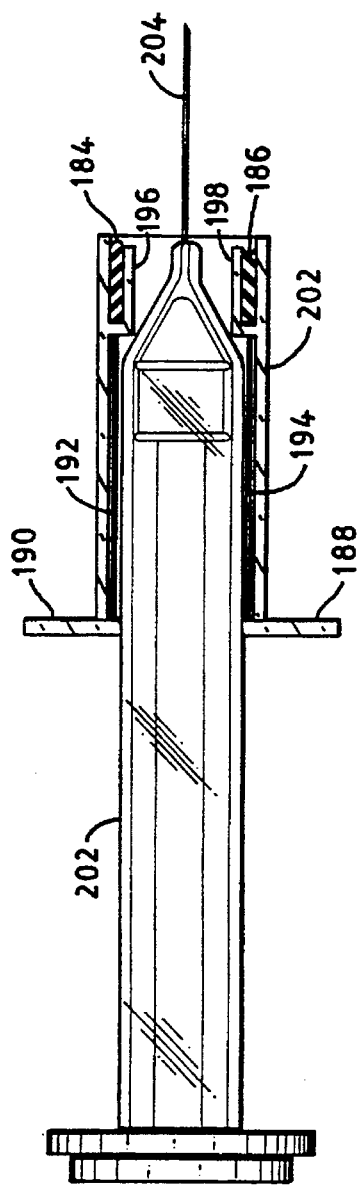

5,593,387

NON-REUSABLE SYRINGE

This is a C-I-P of Ser. No. 08/204,810 filed Mar. 2, 1994 now U.S. Pat. No. 5,419,773.

BACKGROUND OF THE INVENTION

1. Field of the Invention

The present invention is in the field of hypodermic syringes used to inject and aspirate liquid material from a patent. More particularly, this invention is directed to render a syringe non-reusable syringe with an engagable retractable cap for the entire needle.

2. Description of the Prior Art

Hypodermic syringes with attached needles are used for the administration of medication and for the withdrawal of material from a patient. These syringes are generally disposable which presents two problems, one is the possible reuse of a syringe and the other and the greatest danger is the possibility of being pricked by the needle when handling the syringe. These two concerns are particularly important because the needle and/or the syringe may be contaminated and spread disease, such as hepatitis and acquired immune deficiency syndrome (AIDS).

The known non-reusable syringes can easily be reused. In addition, often times needles need to be visible for injection. Some devices provide for a shield where the needles is recessed to prevent possible pricking; however, these devices do not provide for a seal directly over the needle whenever the needle is not in use and the needle is not visible for proper injection. The apparatus of U.S. Pat. No. 4,795,432 to Karczmer does provide a cap at the end of its shield assembly; however, this not only prevents pricking but it also prevents multiple exposure of the needle tip which is sometimes necessary, especially when withdrawing blood for testing. The inventions of U.S. Pat. Nos. 4,507,118 to Dent and 4,767,413 to Haber provide caps but the syringe needle is designed to pass through these caps. Once the needle passes through the caps in these patents, the caps are no longer acting as a complete seal to prevent any leakage.

SUMMARY OF THE INVENTION

In light of the above discussed devices, the present invention provides for a less costly syringe that when full injection has been accomplished, the syringe is non-reusable. This syringe cannot be easily altered to yield a reusable syringe. In addition, the present invention is provided with a shield assembly that contains a permanent cap, one that easily returns to its sealed position, so that whenever the syringe is not in use not only is the needle shielded but it is also capped. The present invention prevents not only the possibility of pricking but also prevents any possibility of leaking.

Accordingly, it is an object of the present invention to provide a non-reusable syringe.

It is another object of present invention to provide a non-reusable syringe with an engagable retractable cap which reseals the needles and prevents pricking and leaking.

It is another object of the present invention to provide a non-reusable syringe with a plunger assembly which operates to lock the syringe in the fully extended position.

BRIEF DESCRIPTION OF THE DRAWING

FIG. 15 is a retractable needle cap and shield assembly.

FIG. 16 is a retracted needle cap and shield assembly.

DESCRIPTION OF THE PREFERRED EMBODIMENT

FIGS. 1–4 show an apparatus for injecting into or withdrawing substances from a patient in the form of a hypodermic syringe.

Figure 1:
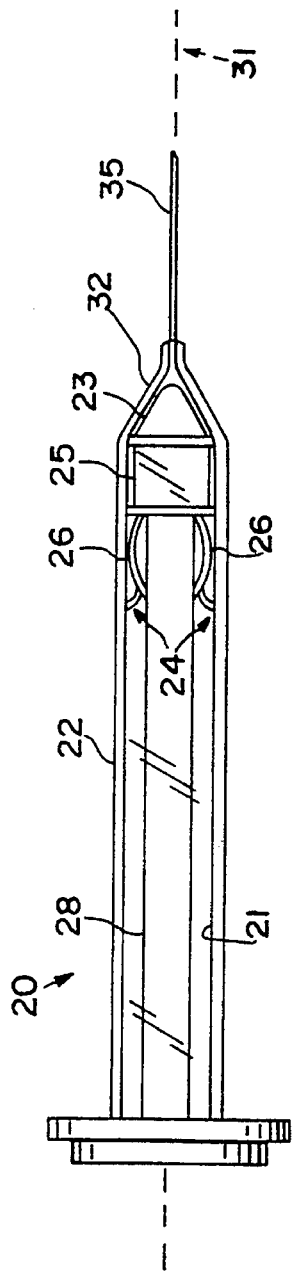
FIG. 1 is a non-reusable disposable syringe before inversion.
Figure 2:
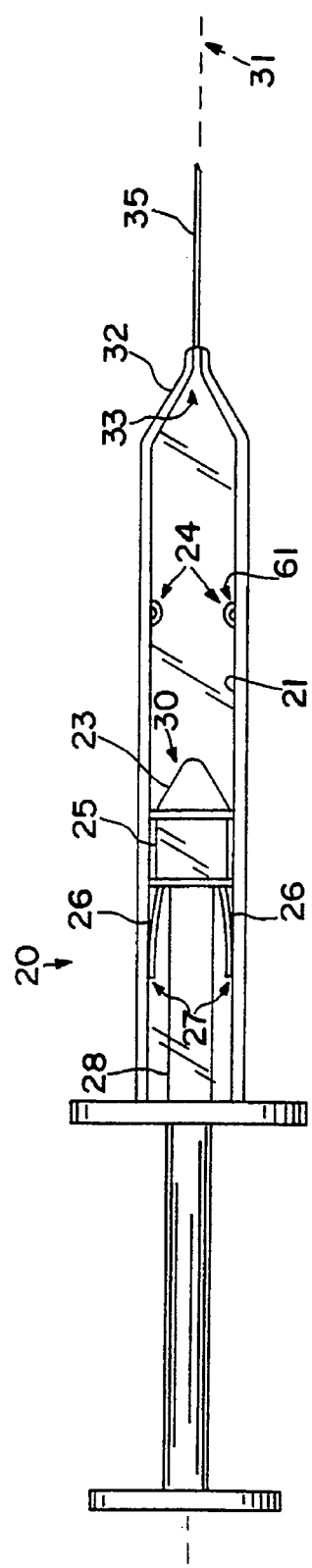
FIG. 2 is a non-reusable disposable syringe during aspiration.
Figure 3:
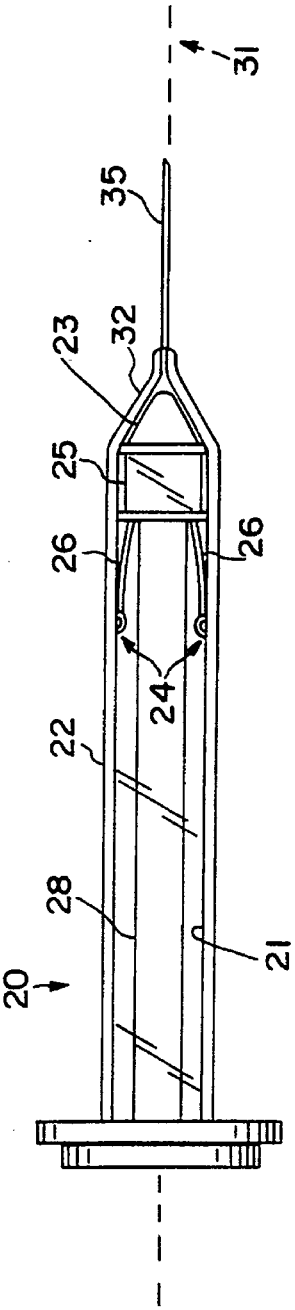
FIG. 3 is a non-reusable disposable syringe fully extended.

FIGS. 1–3 illustrate a preferred embodiment of syringe 20 of the present invention. Syringe 20 includes a tubular cylinder 22 having a head 32 at one end for receiving a needle 35 and an opening (not shown) at the opposite end for receiving a shaft 28 (discussed below).

Tubular cylinder 22 has an inner wall 21. Two curved brackets 24, integral with tubular cylinder 22, extend from inner wall 21 to operate with a plunger in a manner described below.

Syringe 20 also includes a plunger 30 connected on an end of shaft 28. Shaft 28 and plunger 30 travel within tubular cylinder 22 along an axis of travel 31 when aspirating and injecting fluid through opening 33.

Plunger assembly 30 includes a head portion 23 and an integral body portion 25. Head 23 of plunger assembly 30 is configured to fit snugly within head 32 of tubular cylinder 22. As shown in FIGS. 1–3, body 25 has an outer diameter slightly smaller than the inner wall diameter of tubular cylinder 22 to create a vacuum in tubular cylinder 22 during aspiration.

Plunger 30 also includes two outer rims 26 coupled to the rear portion of body 25. As shown in FIGS. 1–3, outer rims 26 extend from the rear portion of body 25 in the direction substantially parallel with the axis of travel. Thus, outer rims 26 are substantially parallel with and proximate to shaft 28. Outer rims 26 have distal ends 27. Outer rims 26 are constructed from flexible material, and tend to extend outwardly away from shaft 28 in their unflexed position. Thus, when plunger 30 is not positioned within tubular cylinder 22, i.e., its unassembled configuration (not shown) the distance between the distal ends 27 is greater than the diameter of inner wall 21 of tubular cylinder 22.

FIG. 1 illustrates the relative location of plunger 30 and tubular cylinder 22 when plunger 30 is initially set in tubular cylinder 22. In this position, curved brackets 24 face toward head 32 to come into contact with outer rims 26. Curved brackets 24 apply a wedge-like pressure against outer rims 26 compressing the outer rims 26 to flex toward shaft 28.

During aspiration, plunger 30 begins at the location shown in FIG. 1 and travels along the axis of travel 31 toward the rear portion of tubular cylinder 22 as shown in FIG. 1. As the body 25 contacts curved brackets 24 during aspiration, it causes curved brackets 24 to invert and point towards the rear portion of syringe 20. As shown in FIG. 2, curved brackets 24 contact inner wall 21 when they are in the inverted position. Curved brackets 24 form a ledge 61 when placed in the inverted position.

When curved brackets 24 do not apply pressure to outer rims 26, outer rims 26 continually press against inner wall 21 of tubular cylinder 22.

Referring to FIG. 3, plunger 30 is in its fully extended position when plunger head 23 is positioned in head 32 of tubular cylinder 22. When plunger 30 reaches this fully extended position, distal ends 27 of outer rims 26 completely pass inverted curved brackets 24. When this occurs, outer rims 26 extend outward to once again press against inner walls 21 of tubular cylinder 22.

Distal ends of outer rims 26 come into contact with ledge 61 of inverted curved brackets 24. Curved brackets 24 work in conjunction with outer rim 26 to prevent plunger assembly 30 from aspirating once plunger assembly 30 has been placed in the fully injected position.

As shown in FIG. 3, curved brackets 24 are located at a position in tubular cylinder 22 such that the complete plunger assembly 30, including outer rims 26, can be positioned between ledge 61 of curved brackets 24 and head 32 of tubular cylinder 22.

In the preferred embodiment of the present invention, there are two curved brackets 24 and two associated outer rims 26. However, as one skilled in the relevant art would find apparent, any number of curved brackets 24 and associated outer rims 26 may be used.

The preferred embodiment is to have the brackets 24 and rim 26 made of metal, the advantage being that it is difficult to remove or file down. In addition, the preferred material of the plunger 30 is rubber. Removal of the metal rim 26 from the rubber plunger 30 would leave holes in the rubber plunger 30 and thereby rendering the syringe useless.

Figure 4:
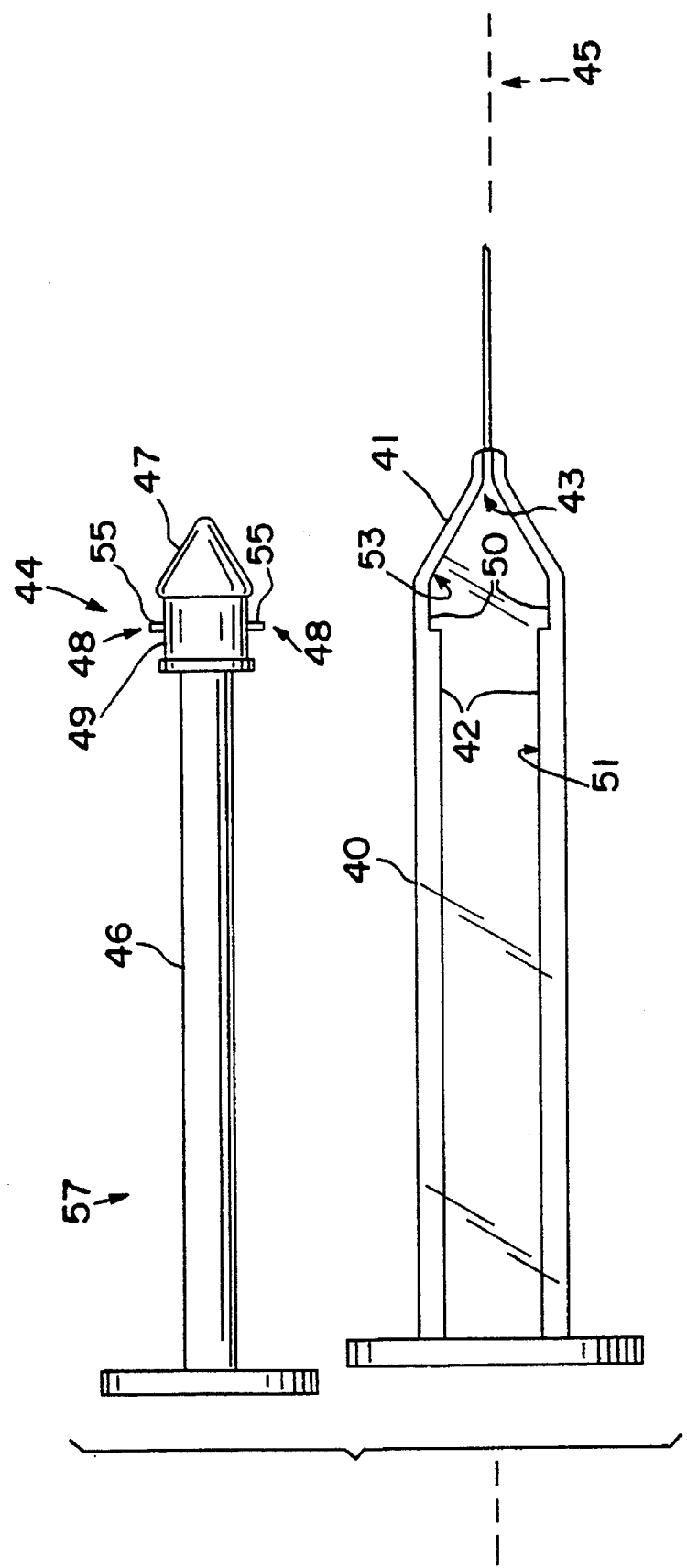
FIG. 4 is a non-reusable disposable syringe assembly.

A second embodiment of the plunger assembly of the present invention is illustrated in FIG. 4. FIG. 4 shows the shaft 46 with a curved plunger assembly 44 and a cylinder 40.

Similar to the embodiment shown in FIGS. 1–3, syringe 57 is comprised of a tubular cylinder 40 having a head 41 at one end for receiving plunger assembly 44 and an opening (not shown) on the opposite end for receiving a shaft 46. Head 41 has an opening 43 configured to receive a needle 35. Syringe 57 also includes a plunger assembly 44 connected on an end of shaft 46. Shaft 46 and plunger 44 travel within tubular cylinder 40 along an axis of travel 45 during aspiration and injection.

The plunger 44 includes an integral head 47 and body 49. Body 49 has an outer diameter slightly smaller than the diameter of inner wall 42 of tubular cylinder 40 to create a vacuum in tubular cylinder 40 during aspiration.

The inner wall 42 of the tubular cylinder 40 has a diameter 51. Tubular cylinder 40 has a depressed area 50 at the end of the tubular cylinder 40 within head 41. As shown in FIG. 4, inner wall 42 has a diameter 53 in depression area 50. The diameter 53 in depression area 50 is greater than diameter 51.

Plunger 44 also includes locking spring assemblies 48 located in plunger body 49. Locking spring assemblies 48 includes internal springs located within body 49 (now shown), and spring shafts 55 extending from body 49 in a direction substantially perpendicular to the axis of travel 45. The configuration and operation of locking spring assembly 48 is considered to be well known to one of ordinary skill in the art. When plunger 44 is in its fully extended position, the internal springs (not shown) cause the spring shafts 55 to extend outward to contact the inner wall of the tubular cylinder 40 in depressed area 50. Thus, the spring shafts 55 work in conjunction with the depressed area 50 to prevent the plunger 44 from aspirating once the plunger 44 has been placed in its fully extended position.

Like the metal rim 26 of FIG. 3, removal of the locking springs 48 would damage the rubber plunger 44 and make it impossible to retain fluid in the syringe.

Figure 5:
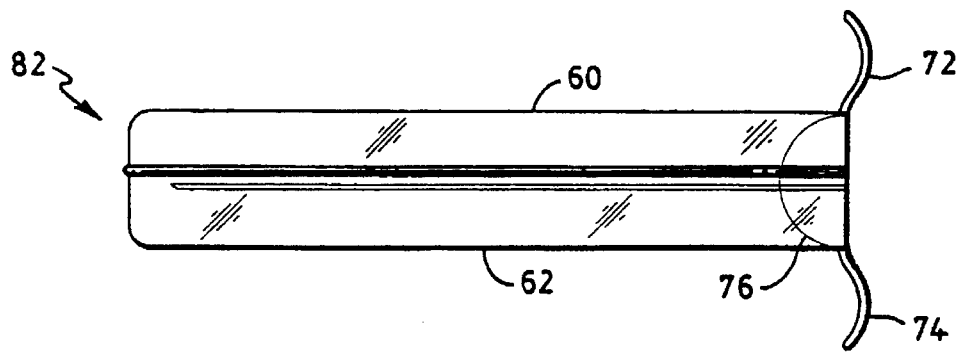
FIG. 5 is a protective needle cap.
Figure 6:
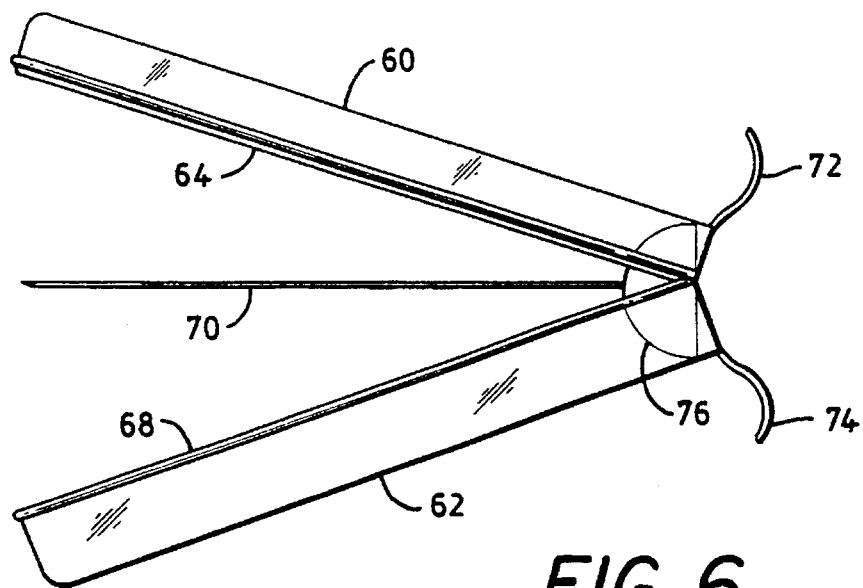
FIG. 6 is a opened protective needle cap.
Figure 7:
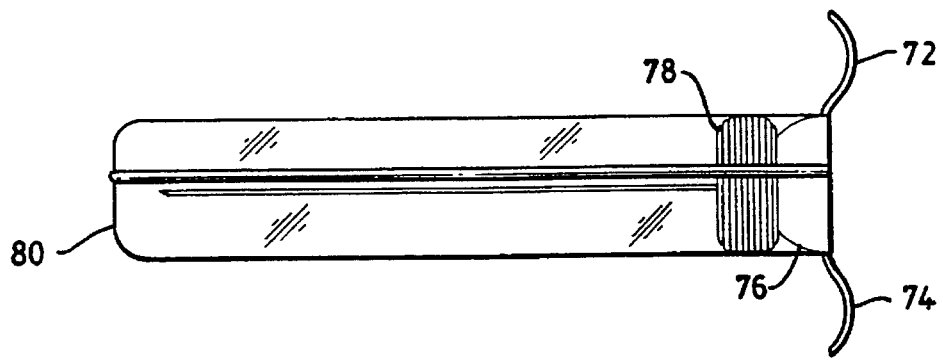
FIG. 7 is a clamped protective needle cap.

In order that a non-reusable syringe may not be a threat to society, the needle of the syringe must likewise be rendered safe. FIGS. 5–7 show the preferred embodiments of a non-removable cap for a needle. The cap may be attached to a needle that is permanently affixed to a syringe or it may be attached separately.

The preferred material used for the cap 82 is a rigid, clear plastic. The cap consists of two half cylinders 60 and 62. Each half cylinder having either a rubber male 64 or female 66 fitting assure a tight closure around a sterile needle 70. On each end of the cylinder halves 60 and 62 are extension tabs 72 and 74.

At the base of the needle 70, the preferred embodiment is a rubber lower seal 76 to ensure fit with rubber ports of medication 78.

Pressure is exerted on the tabs 72 and 74 which forces the cylinder halves 60 and 64 to open exposing the needle 70, FIG. 6. Releasing the pressure from the extension tabs 72 and 74 automatically reseals the cap 82, FIG. 7.

The advantage of the above described embodiment in FIG. 7, is that when medication is being administered for a period of time, the pressure is released from the extension tabs 72 and 74 and the half cylinders 60 and 62 of the cap act as a clamp which ensures that the needle will not easily slip out of position, and even if it should, the cap would automatically close over the end of the needle 70 and the needle 70 would not be a threat to anyone in the vicinity.

Figure 7A:
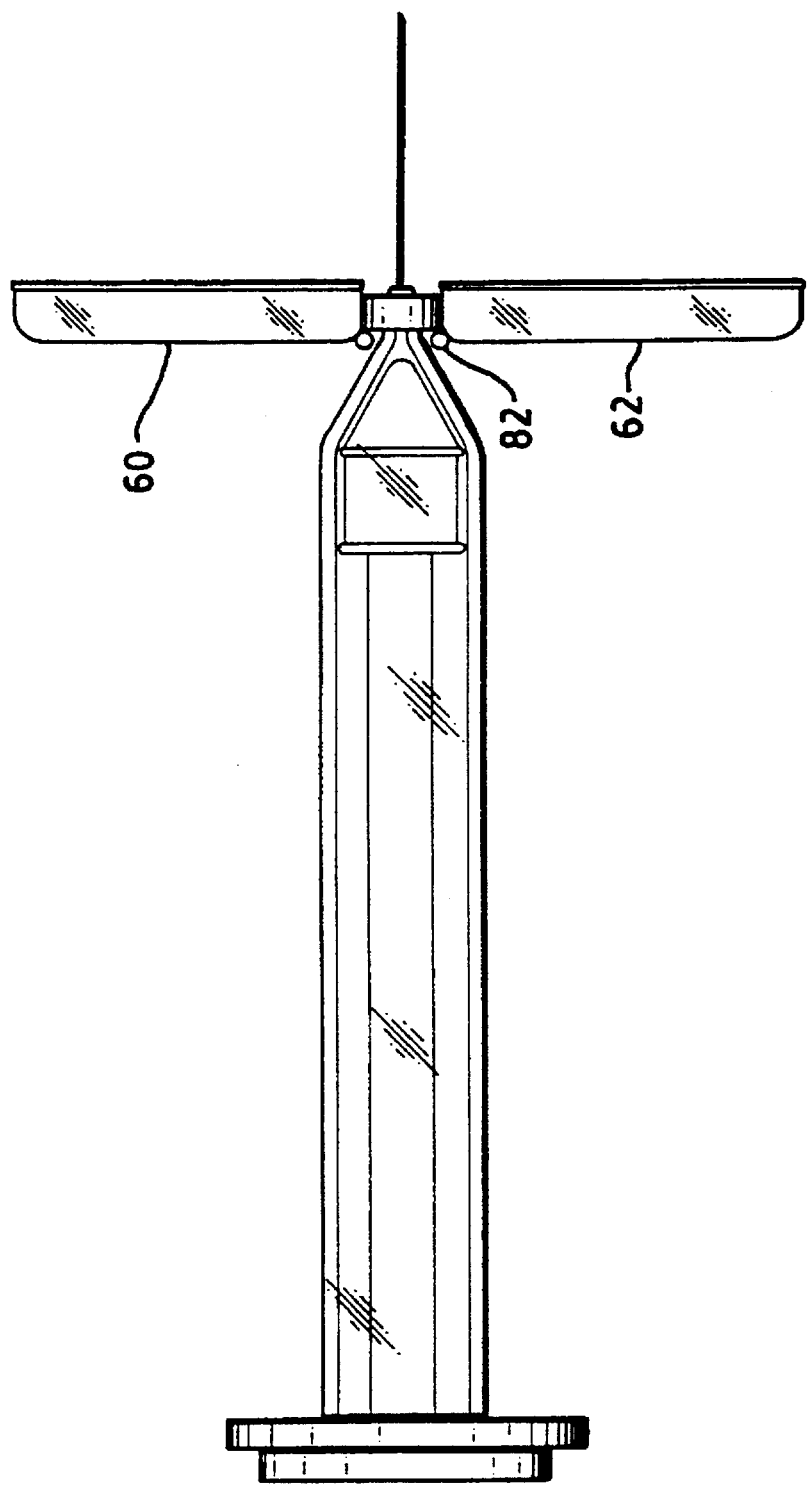
FIG. 7A is a non-reusable disposable syringe assembly having an opened protective needle cap.

Another variation of FIGS. 5–7 would be to have a spring device 82 as seen in FIG. 7a rather than the extension tabs 72 and 74. Pressure can be exerted on the spring devices 82 which would force the cylinders 60 and 62 to open. The spring devices 82 can be locked in place so that the needle is fully visible for injection or may be released once the needle is positioned on tubing so as to form a clamp.

Figure 8:
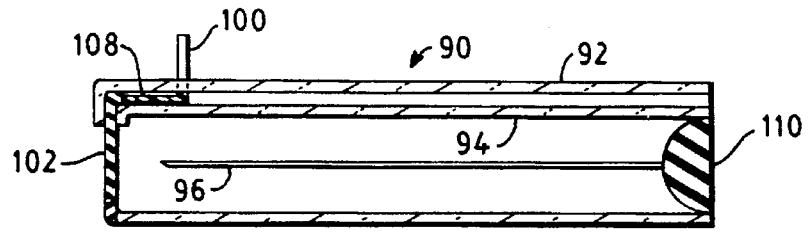
FIG. 8 is a retractable protective needle cap.
Figure 9:
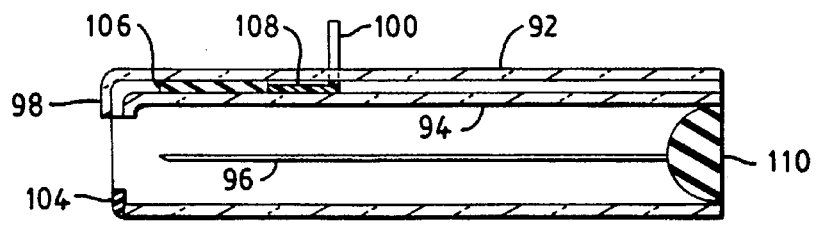
FIG. 9 is a retracted protective needle cap.
Figure 10:
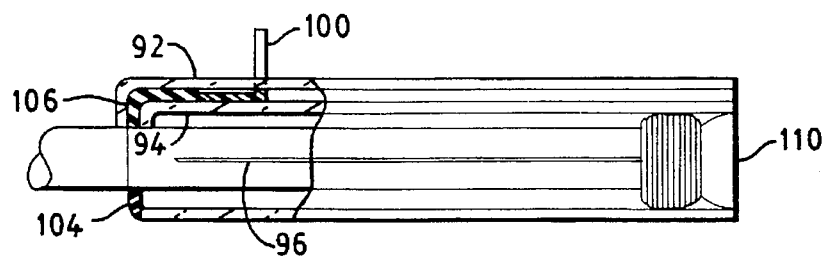
FIG. 10 is a retracted protective needle cap in a clamp position.

FIGS. 8–10 illustrates a variation of the needle protector cap assembly (cap and shield assembly) with a preferred embodiment that is made of a rigid cylinder 90 of clear plastic with an inner 92 and outer 94 wall that extends beyond the needle tip 96. The outer wall 94 extends slightly beyond and around the inner wall 92, forming a lip 98 over the inner wall 92, FIG. 9. The outer wall also has an opening (not shown) that runs partially along the side of the shield to allow a lever 100 to be pushed down alongside.

The cap 102 of the preferred shield assembly is made of rubber. The cap 102, as can be seen in FIG. 9, is in two sections 104 and 106. Each section has either a rubber male or female fitting to assure a tight closure around a sterile needle. Once cap section 104 is firmly affixed to the end of the cylinder 90. The other section 106 is attached to the lever 100 through tension means 108. When the lever 100 is pushed towards the base 110 of the needle 96 the cap section 104 easily slides between the outer 94 and the inner 92 wall.

When the lever 100 is released the retracted cap section 104 returns to its closed position FIG. 10. The lip 98 allows the cap 104 to return to its proper closed position. The advantages of such an embodiment is that the needle is always in a recessed position so that injury as the result of pricking can be avoided, when pressure is released from the lever 100, the needle is either resealed, or when medication if being administered, the cap acts as a clamp which ensures that the needle will not easily slip out of position during administration. This embodiment is also advantageous for Y ports or for Heparin locks.

Figure 11:
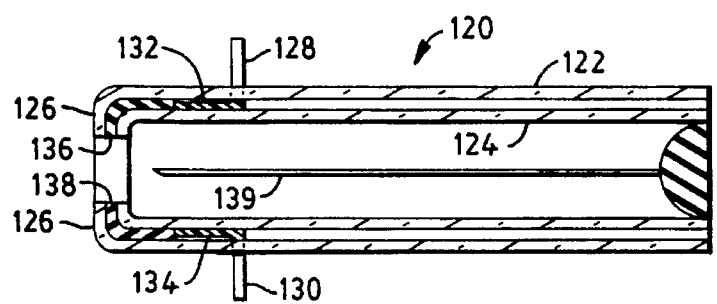
FIG. 11 is a dual retractable protective needle cap.

A shield assembly in which both sections of the cap 136 and 138 are retractable is demonstrated in FIG. 11. In this embodiment, the shield assembly 120 is defined by a double walled thickness cylinder. The outer wall 122 extends beyond and over the inner wall 124 forming a lip 126. The sharp end of the needle 139 is recessed within the cylinder 120. On opposite sides of the cylinder there are two tracks (not shown) cut out of the outer wall 122 to allow the levers 128 and 130 to slide alongside the cylinder 120.

Each cap section 136 and 138 is attached to tension means 132 and 134 which is attached to corresponding lever 128 and 130. When pressure is exerted upon the levers 128 and 130, the cap sections 136 and 138 pull back between the inner 124 and outer walls 122 of the cylinder. Upon releasing the levers 128 and 130, the cap sections 136 and 138 automatically return to the sealed position.

The advantage of both cap sections 136 and 138 being retractable is that a more uniform clamp can be attained when administrating medications.

Figure 12:
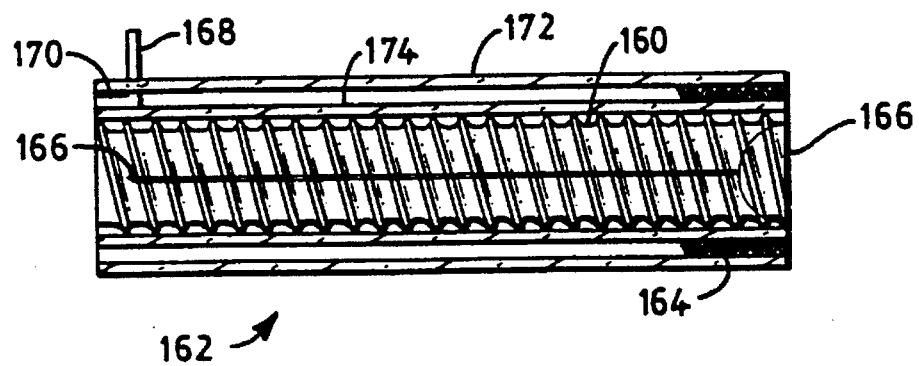
FIG. 12 is a retractable protective needle cap.
Figure 13:
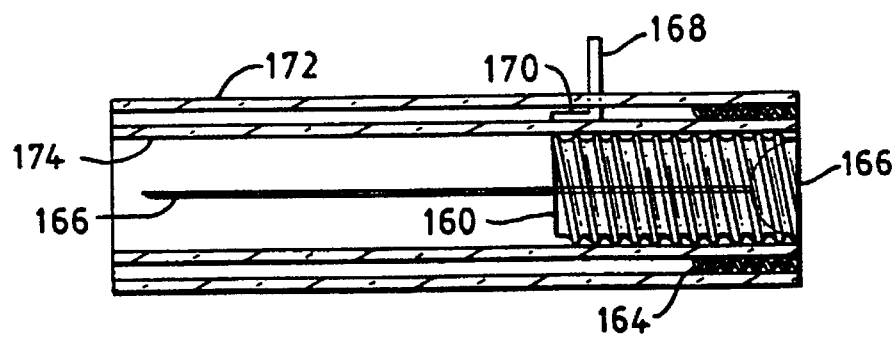
FIG. 13 is a retracted protective needle cap.

Another for a retractable cap as described above can be seen in FIGS. 12 and 13. This embodiment has the permanent cap consisting of either one or two sides of corrugate-like tubing 160 that is joined to the lever 168 through tension means 170. The lever 168 slides between the outer 172 and the inner 174 wall of the cylinder 162. The cylinder 162 is affixed to the syringe ad is made of clear plastic. At the base of the needle 166, there is a spring apparatus 164. The spring apparatus 164 is necessary to create a firm pressure seal around a port to prevent pulling out the needle. When the lever 168 is pulled back, the corrugated-like tubing 160 folds back and exposes the needle 166 for insertion, FIG. 13. When the lever 168 is released, the corrugated tubing 160 springs back and forms a seal around the needle 166 port, FIG. 12. A dual retractable cap as described above can be similarly employed.

Figure 14:
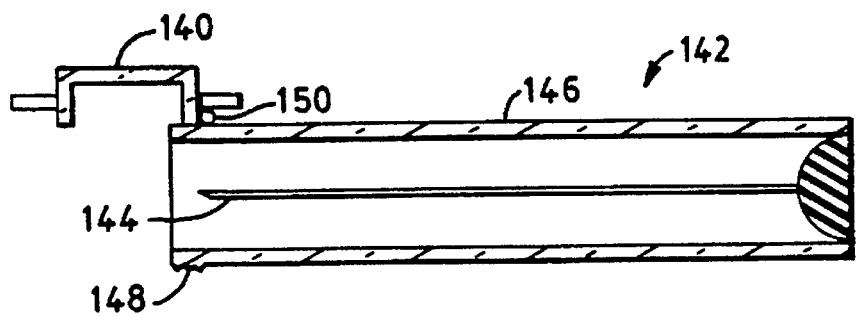
FIG. 14 is a removable protective needle cap.

The permanent cap illustrated in FIG. 14 is a cap 140 that can hinged 150 onto the cylinder 142. When the needle 144 is to be used, the cap 140 can be released from the cylinder while it is still attached on one side 150 of the cylinder 140. While the needle 144 is in use, the cap 140 can be fastened alongside the cylinder 146. When through with the needle 144, the cap 140 can be released and fastened at its close position 148.

There are instances where the length of the needle must be exposed for use, such as when medication is being administered directly into a patient or body fluid is being withdrawn. This being the case, a shield assembly is necessary that retracts entirely along the length of the needle.

A retractable cap and shield assembly is demonstrated in FIGS. 15 and 16. The cap 180 is made of a rubber substance and the sides of the assembly (cylinder) 182 is made of a more clear durable plastic. The cap sections 184 and 186 have a rubber male—female fitting and are attached to the levers 188 and 190 through tension means 192 and 194. As the cap sections 184 and 186 are pulled back, they retract into compartments 196 and 198 along the outer wall 200 of the assembly on either side of the needle 204. Once the cap sections 184 and 186 are in the compartments 196 and 198, additional pressure of the tension means 192 and 194 causes the outer wall 200 of the durable plastic assembly to retract over the inner wall 202 of the assembly, thereby exposing the needle 204, FIG. 16. When the needle 204 is exposed, the levers 188 and 190 can be locked in place in grooves 206 and 208 along the side of the inner wall 202 of the assembly. When the levers 188 and 190 are released, the assembly automatically reseals over the needle 204, FIG. 15.

Figure 17:
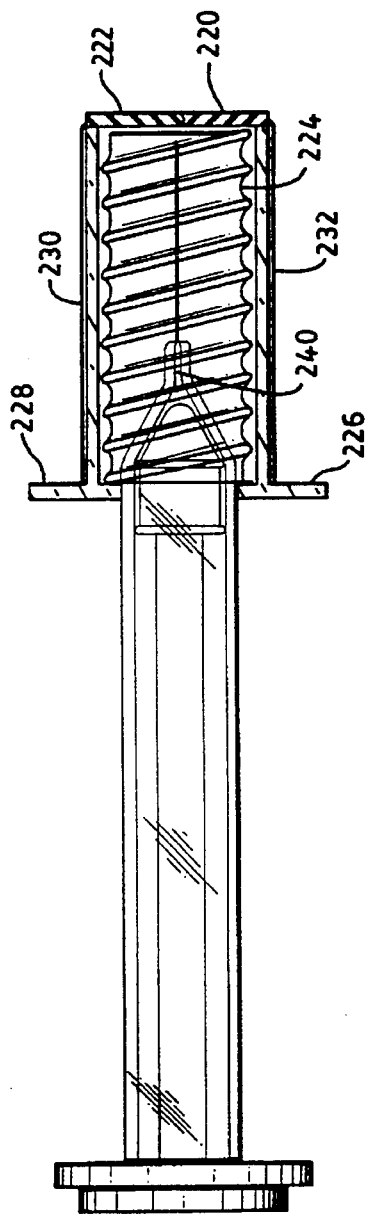
FIG. 17 is a retractable needle cap and shield assembly.
Figure 18:
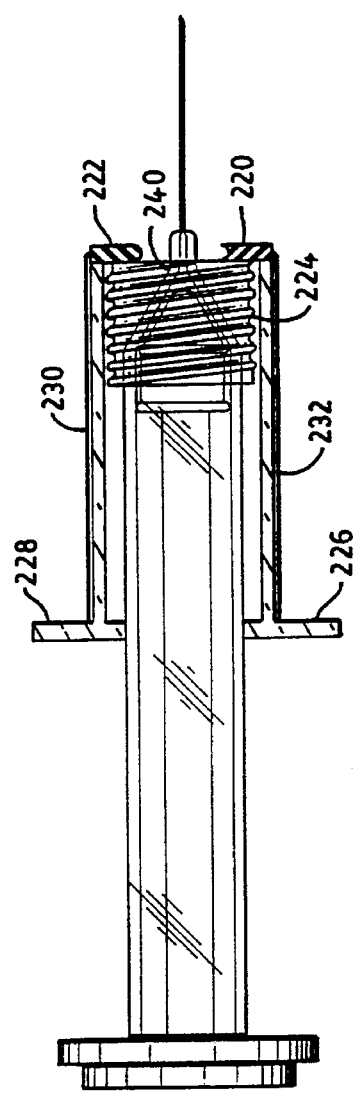
FIG. 18 is a retracted needle cap and shield assembly.

Another variation of the above described shield assembly is seen in FIGS. 17 and 18. The cap sections 220 and 222 are made of rubber and are attached to corrugated-like tubing 224 which is attached to levers 226 and 228 through tension means 230 and 232. When pressure is applied to the levers 226 and 228, the rubber cap sections 220 and 222 are retracted until they are stopped against the wall of the corrugated-like tubing 224, FIG. 17. Additional pressure on the levers 226 and 228 causes the corrugated-like tubing 224 to fold back at the base of the needle 240, FIG. 18. Once the desired needle 240 exposure is attained, the levers 226 and 228 can be secured in the grooves 234 and 236 along the clear plastic wall 238 of the assembly. When the levers 226 and 228 are released, the assembly automatically reseals over the needle 240, FIG. 17.

While the foregoing invention has been described with references to its preferred embodiments, it should not be limited to such embodiments since various alterations and modifications will occur to those skilled in the art. For example, the plastic and rubber materials used could be replaced by equally effective materials. All such variations and modifications are intended to fall within the scope of the appended claims:

What is claimed:

1. A non-reusable syringe comprising:

a hollow tubular cylinder including an inner wall having a first diameter and an opening at one end for the entering and exiting of fluids;

a curved bracket extending from said inner wall of said cylinder;

a plunger attached to a shaft within said cylinder, said plunger adapted to travel along an axis of travel between a fully extended position in which the head of the plunger is adjacent to a rear end of the cylinder to a fully depressed position in which the head of the plunger is adjacent to a front end of the cylinder; and a flexible rim extending from a rear portion of said plunger along the axis of travel, said flexible rim continually extending outwardly from said plunger to a distal end having a second diameter greater that said first diameter when said rim is in an un-flexed position;

wherein when said plunger is initially positioned at said fully depressed position said curved bracket operates in conjunction with said outer rim to prevent said plunger from being permanently secured in said fully depressed position;

wherein when said plunger is pulled from said initial position toward said fully extended position said plunger inverts said curved brackets; and whereafter said curved bracket operates in conjunction with said outer rim to lock said plunger in place when said plunger is subsequently positioned in said fully depressed position.

\* \* \* \* \*